US00PP12647P2

(12) United States Plant Patent
Nygaard

(10) Patent No.: US PP12,647 P2
(45) Date of Patent: May 28, 2002

(54) PENTAS PLANT NAMED 'POLARIS'

(75) Inventor: Ib Nygaard, Odense SO (DK)

(73) Assignee: D. S. Cole Growers, Inc., Loudon, NH (US)

( * ) Notice: Subject to any disclaimer, the term of this patent is extended or adjusted under 35 U.S.C. 154(b) by 0 days.

(21) Appl. No.: 09/624,470

(22) Filed: Jul. 24, 2000

(51) Int. Cl.[7] ..... A01H 5/00
(52) U.S. Cl. ..... Plt./263
(58) Field of Search ..... Plt./263

(56) References Cited

PUBLICATIONS

UPOV–ROM GTITM Computer Database 2001/02, Apr. 2, 2001, GTI Jouve Retrieval Software, Citation for Pentas 'Polaris'.*

* cited by examiner

*Primary Examiner*—Bruce R. Campell
*Assistant Examiner*—June Hwu
(74) *Attorney, Agent, or Firm*—C. A. Whealy

(57) ABSTRACT

A distinct cultivar of Pentas plant named 'Polaris', characterized by its uniform and compact plant habit; freely branching habit; numerous white-colored flowers; and suitability for container production.

1 Drawing Sheet

BACKGROUND OF THE INVENTION

The present Invention relates to a new and distinct cultivar of Pentas plant, botanically known as *Pentas lanceolata*, and hereinafter referred to by the cultivar name Polaris.

The new Pentas is a product of a planned breeding program conducted by the Inventor in Odense, Denmark. The new Pentas originated from a self-pollination made by the Inventor of the *Pentas lanceolata* cultivar Juniper, not patented. The new Pentas was selected in a controlled environment from the resulting progeny by the Inventor in early 1998, on the basis of its white-colored flowers and suitability for container production.

Asexual reproduction of the new cultivar by terminal cuttings taken in Odense, Denmark has shown that the unique features of this new Pentas are stable and reproduced true to type in successive generations.

SUMMARY OF THE INVENTION

Plants of the cultivar Polaris have not been observed under all possible environmental conditions. The phenotype may vary somewhat with variations in environment such as temperature, light intensity, daylength, water status, and fertility level without, however, any variance in genotype.

The following traits have been repeatedly observed and are determined to be the unique characteristics of 'Polaris'. These characteristics in combination distinguish 'Polaris' as a new and distinct cultivar:

1. Uniform and compact plant habit.
2. Freely branching habit.
3. Numerous white-colored flowers.
4. Suitable for container production.

Plants of the new Pentas differ from plants of its parent cultivar, Juniper, and plants of its sibling cultivars Comet, disclosed in U.S. Plant patent application Ser. No. 09/624,468, Mars, disclosed in U.S. Plant patent application Ser. No. 09/624,469; and Venus, disclosed in U.S. Plant patent application Ser. No. 09/624,407, primarily in flower color.

Plants of the new Pentas can be compared to plants of the cultivar Blushing Beauty, not patented. Plants of the new Pentas differ from plants of the cultivar Blushing Beauty in the following characteristics:

1. Leaves of the new Pentas are more intense green and glossier than leaves of the cultivar Blushing Beauty.
2. Plants of the new Pentas have larger inflorescences than plants of the cultivar Blushing Beauty.
3. Petal color of the new Pentas is pure white whereas petal color of the cultivar Blushing Beauty is white and tinged with pink.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Pentas.

The photograph at the top of the sheet comprises a top perspective view of a typical plant of 'Polaris'.

The photograph at the bottom of the sheet comprises a close-up view of typical flowers of 'Polaris'.

DETAILED BOTANICAL DESCRIPTION

In the followig description, color references are made to The Royal Horticultural Society Colour Chart except where general terms of ordinary dictionary significance are used. Plants grown in 10-cm containers were used for the following description. Plants were grown under conditions which closely approximate commercial production conditions in Loudon, N.H. Plants used for the description were about 8 weeks old.

Botanical classification: *Pentas lanceolata* cultivar Polaris.
Parentage: Self-pollination of *Pentas lanceolata* cultivar Juniper, not patented.
Propagation:
*Type cutting*.—Terminal vegetative cuttings.
*Time to initiate roots*.—About 12 to 14 days at 21° C.
*Time to develop roots*.—About 30 days at 21° C.

*Root description.*—Numerous, fibrous and well-branched.

Plant description:

*Form.*—Annual flowering plant; upright, somewhat outwardly spreading, uniform, rounded inverted triangle; dense and full, freely branching with about six lateral branches per plant, pinching enhances lateral branch development. Appropriate for 10-cm containers.

*Crop time.*—About 6 to 8 weeks are required to produce finished flowering plants in 10-cm containers.

*Plant height.*—About 38 cm.

*Plant diameter.*—About 34 cm.

*Growth rate.*—Moderate.

*Vigor.*—Moderately vigorous.

*Lateral branches.*—Length: About 15 cm. Diameter: About 2.5 mm. Internode length: About 4 cm. Strength: Moderate. Texture: Pubescent. Color: 144C.

*Foliage description.*—Leaves simple, generally symmetrical and long-persisting; opposite. Quantity per lateral branch: About 10. Length: About 9 cm. Width: About 4 cm. Shape: Lanceolate. Apex: Acute. Base: Acute. Margin: Entire. Aspect: Typically horizontal. Texture: Slightly rugose; pubescent. Color: Young foliage, upper surface: 139A. Young foliage, lower surface: 138B. Mature foliage, upper surface: 147A, veins, 145B. Mature foliage, lower surface: 146B, veins, 145C. Petiole length: About 1.25 mm. Petiole diameter: About 1 mm. Petiole color: 145C.

Flower description:

*Flower type and habit.*—Single flowers arranged in terminal corymbs; five-merous; flowers face mostly upward; aspect, mostly flat. Flowers persistent. Very freely flowering, typically about 40 flowers per inflorescence, about six inflorescences per plant, and about 240 open flowers and flower buds per plant.

*Natural flowering season.*—Summer; flowering continuous.

*Flower longevity on the plant.*—About two weeks.

*Fragrance.*—None detected.

*Inflorescence size.*—Diameter: About 8 cm. Height: About 5 cm.

*Flower size.*—Diameter: About 1.5 cm. Height (tube length): About 5 mm.

*Flower buds.*—Rate of opening: About one week. Length: About 0.5 to 2 cm. Diameter: About 2.5 to 5 mm. Shape: Spatulate. Color: 155A.

*Corolla.*—Arrangement/appearance: Single whorl of five petals, fused at base, flaring into a star. Petal length from throat: About 5 mm. Petal width: About 3.3 mm. Petal shape: Ovate. Petal apex: Acute. Petal margin: Entire. Petal texture: Smooth, dull. Color: Petal, upper surface, when opening: 4C. Petal, lower surface, when opening: 155B. Petal, upper surface, fully opened: 155B to 155C. Petal, lower surface, fully opened: 155B.

*Sepals.*—Arrangement/appearance: Single whorl of five sepals, star-shaped. Calyx length: About 2.5 mm. Calyx diameter: About 1 cm. Shape: Lanceolate. Apex: Acute. Margin: Entire. Texture: Smooth. Color, upper and lower surfaces: 147A.

*Peduncles.*—Length: About 1 cm. Angle: Erect. Strength: Moderately strong. Texture: Smooth. Color: 144A.

*Reproductive organs.*—Stamens: Quantity: About five. Anther shape: Filiform. Anther length: About 1.25 mm. Anther color: 161C. Pollen amount: Scarce. Pollen color: 161C. Pistils: Quantity: One. Pistil length: About 2.5 cm. Stigma shape: V-shaped. Stigma color: 157C. Style length: About 2 cm. Style color: 157A. Ovary color: 145C.

*Seed/fruit.*—Seed/fruit production has not been observed.

Disease resistance: Plants of the new Pentas have been observed to be resistant to pathogens common to Pentas.

It is claimed:

1. A new and distinct cultivar of Pentas plant named 'Polaris', as illustrated and described.

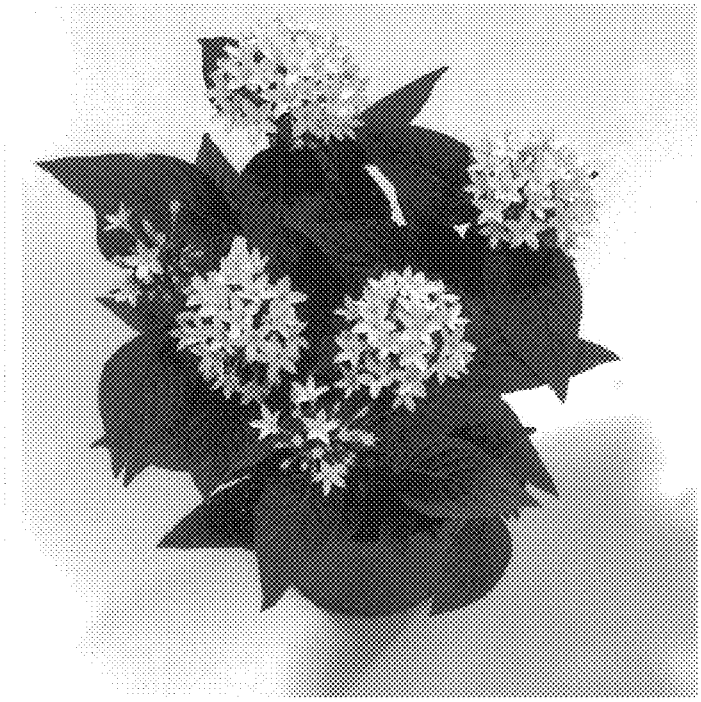
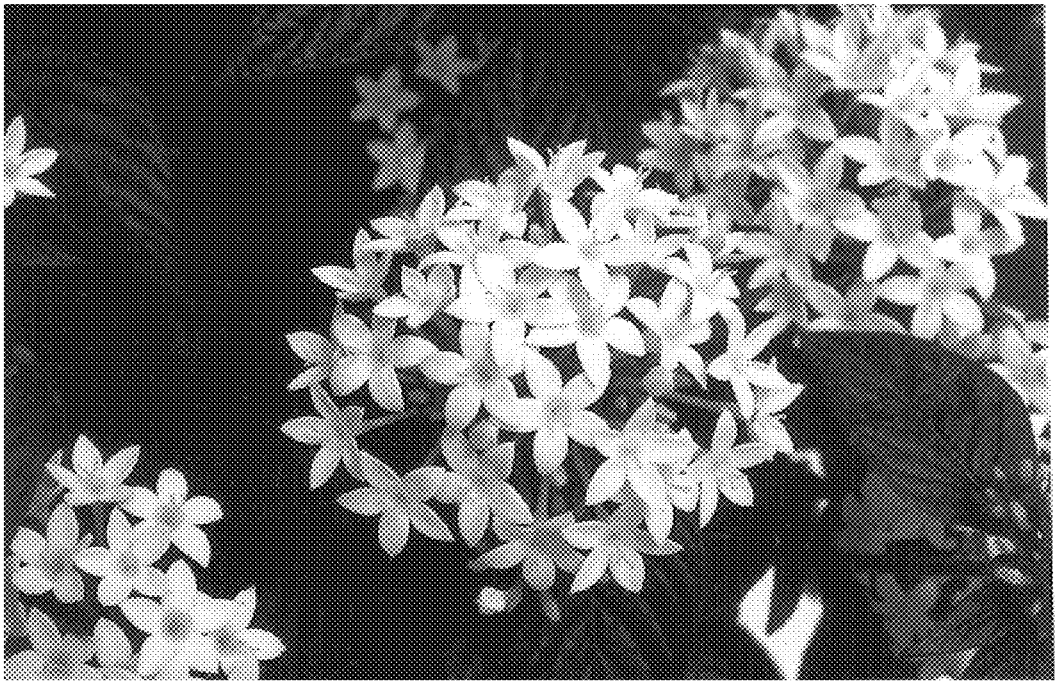

* * * * *